United States Patent [19]
Berg

[11] Patent Number: 5,258,102
[45] Date of Patent: * Nov. 2, 1993

[54] SEPARATION OF HEPTANE FROM VINYL ACETATE BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[*] Notice: The portion of the term of this patent subsequent to Oct. 26, 2010 has been disclaimed.

[21] Appl. No.: 38,289

[22] Filed: Mar. 29, 1993

[51] Int. Cl.$^5$ .......................... B01D 3/36; C07C 7/08; C07C 67/54

[52] U.S. Cl. ...................................... 203/60; 203/62; 203/63; 203/DIG. 10; 560/248; 585/860; 585/862; 585/864; 585/866

[58] Field of Search ............ 203/60, 62, 63, DIG. 10; 560/248; 585/860, 862, 864, 866

[56] References Cited

U.S. PATENT DOCUMENTS

| | | | |
|---|---|---|---|
| 3,394,057 | 7/1968 | Miller et al. | 203/DIG. 10 |
| 3,691,021 | 9/1972 | Feldman et al. | 560/248 |
| 3,736,236 | 5/1973 | Di Fiore et al. | 560/248 |
| 4,897,161 | 1/1990 | Berg et al. | 203/51 |
| 4,925,533 | 5/1990 | Berg | 203/51 |

Primary Examiner—Wilbur Bascomb, Jr.

[57] ABSTRACT

Heptane cannot be separated from vinyl acetate by conventional distillation or rectification because of the minimum boiling azeotrope. Heptane can be readily separated from vinyl acetate by using azeotropic distillation. Typical examples of effective agents are methyl acetate, ethanol, ethyl formate or t-amyl methyl ether.

2 Claims, No Drawings

SEPARATION OF HEPTANE FROM VINYL ACETATE BY AZEOTROPIC DISTILLATION

FIELD OF THE INVENTION

This invention relates to a method for separating heptane from vinyl acetate using certain organic compounds as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

Heptane, B.P.=98.4° C. and vinyl acetate, B.P.=72.7° C. form a minimum azeotrope boiling at 72° C. and containing 83.5% vinyl acetate and therefore are impossible to separate by distillation or rectification. Azeotropic distillation would be an attractive method to break this azeotrope and separate heptane from vinyl acetate by rectification.

TABLE 1

| Theoretical and Actual Plates Required vs. Relative Volatility for Heptane - Vinyl Acetate Separation | | |
|---|---|---|
| Relative Volatility | Theoretical Plates Required At Total Reflux, 99% Purity | Actual Plates Required 75% Plate Efficiency |
| 1.2 | 51 | 68 |
| 1.5 | 23 | 31 |
| 2.0 | 13 | 17 |
| 2.3 | 11 | 15 |
| 2.5 | 10 | 13 |

The advantage of using azeotropic distillation in this separation can be seen from the data shown in Table 1. If an agent can be found that will increase the relative volatility to 2.5, only thirteen actual plates will be required to produce 99% purity.

OBJECTIVE OF THE INVENTION

The objects of this invention are to provide a process or method of azeotropic distillation that will enhance the relative volatility of heptane to vinyl acetate in their separation in a rectification column. It is a further object of this invention to identify certain organic compounds which are effective as azeotropic distillation agents, that are stable and can be readily separated from heptane and vinyl acetate and can be recycled to the azeotropic distillation column with little decomposition.

SUMMARY OF THE INVENTION

The objects of the invention are provided by a process for the separation of heptane from vinyl acetate which entails the use of certain organic compounds as the agent in azeotropic distillation.

DETAILED DESCRIPTION OF THE INVENTION

I have discovered that certain organic compounds will effectively increase the relative volatility between heptane and vinyl acetate by rectification when employed as the agent in azeotropic distillation.

TABLE 2

| Effective Azeotrope Formers To Separate Heptane From Vinyl Acetate | |
|---|---|
| Compounds | Relative Volatility |
| Acetone | 1.21 |
| Ethanol | 2.15 |
| Acetonitrile | 1.17* |
| Methyl acetate | 2.3 |
| Ethyl formate | 2.5 |
| t-Amyl methyl ether | 1.95 |

*Brings heptane out as overhead

Table 2 summarizes the data obtained with these agents in a rectification column. The agents which are effective are acetone, ethanol, acetonitril methyl acetate, ethyl formate and t-amyl methyl ether.

THE USEFULNESS OF THE INVENTION.

The usefulness or utility of this invention can be demonstrated by referring to the data presented in Tables 1.and 2. All of the successful agents show that heptane can be separated from vinyl acetate by means of azeotropic distillation in a rectification column and that the ease of separation as measured by relative volatility is considerable.

WORKING EXAMPLES

Example 1:

Eighty grams of heptane, 20 grams of vinyl acetate and fifty grams of acetonitrile were charged to a glass perforated plate rectification column containing 7.3 theoretical plates. After three hours at total reflux, overhead and bottoms samples were taken and analyzed by gas chromatography. The overhead was 16.8% heptane, 3.1% vinyl acetate and 80.1% acetonitrile; the bottoms was 34.3% heptane, 20.0% vinyl acetate and 45.7% acetonitrile which is a relative volatility of heptane to vinyl acetate of 1.17.

Example 2:

Eighty grams of heptane, 20 grams of vinyl acetate and fifty grams of ethyl formate were charged to the glass perforated plate rectification column containing 7.3 theoretical plates. After eight hours at total reflux, overhead and bottoms samples were taken and analyzed. The overhead was 26.5% heptane, 42.8% vinyl acetate and 30.6% ethyl formate; the bottoms was 99.8% heptane, 0.2% vinyl acetate and 0% ethyl formate. This indicates a relative volatility of vinyl acetate to heptane of 2.5.

I claim:

1. A method for recovering heptane from a mixture of heptane and vinyl acetate which comprises distilling a mixture of heptane and vinyl acetate in the presence of an azeotrope forming agent, recovering the heptane and the azeotrope forming agent as overhead product and obtaining vinyl acetate from the stillpot, wherein said azeotrope forming agent is acetonitrile.

2. A method for recovering vinyl acetate from a mixture of vinyl acetate and heptane which comprises distilling a mixture of vinyl acetate and heptane in the presence of an azeotrope forming agent, recovering the vinyl acetate and the azeotrope forming agent as overhead product and obtaining the heptane from the still-pot, wherein said azeotrope forming agent comprises a material selected from the group consisting of acetone, ethanol, methyl acetate, ethyl formate and t-amyl methyl ether.

* * * * *